(12) United States Patent
Fetzer et al.

(10) Patent No.: US 7,562,576 B2
(45) Date of Patent: Jul. 21, 2009

(54) CONVENIENT ULTRASONIC INSPECTION DEVICE

(75) Inventors: Barry A. Fetzer, Renton, WA (US); Jeffrey R. Kollgaard, Kent, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 272 days.

(21) Appl. No.: 11/608,018

(22) Filed: Dec. 7, 2006

(65) Prior Publication Data

US 2007/0084290 A1   Apr. 19, 2007

Related U.S. Application Data

(63) Continuation-in-part of application No. 10/870,962, filed on Jun. 21, 2004, now Pat. No. 7,222,514.

(51) Int. Cl.
*G01N 29/04* (2006.01)
(52) U.S. Cl. .................. 73/614; 73/588; 73/632
(58) Field of Classification Search .............. 73/588, 73/614, 629, 632, 644
See application file for complete search history.

(56) References Cited

U.S. PATENT DOCUMENTS

| | | | |
|---|---|---|---|
| 3,640,122 A * | 2/1972 | Nusbickel, Jr. .............. 73/609 |
| 3,813,926 A | 6/1974 | Stubbeman | |
| 4,184,373 A * | 1/1980 | Evans et al. ................... 73/588 |
| 4,215,583 A | 8/1980 | Botsco et al. | |
| 4,760,738 A * | 8/1988 | Katamine ..................... 73/644 |
| 4,840,066 A | 6/1989 | Botsco et al. | |
| 4,879,796 A | 11/1989 | Nakamura et al. | |
| 4,897,796 A | 1/1990 | Salvado | |
| 5,163,027 A | 11/1992 | Miller et al. | |
| 5,618,994 A | 4/1997 | Falsetti | |
| 6,073,477 A | 6/2000 | Woodmansee et al. | |
| 2005/0279171 A1 | 12/2005 | Kollgaard et al. | |

FOREIGN PATENT DOCUMENTS

DE      299 08 615 U 1        6/2000

OTHER PUBLICATIONS

Imaeva, L.A., et al., "Ultrasound Inspection of Multilayered Cellular Structures Produced By Superplastic Forming and Diffusion Bonding", vol. 15, No. 11, 2001, pp. 895-897.

* cited by examiner

*Primary Examiner*—John E Chapman
(74) *Attorney, Agent, or Firm*—Alston & Bird LLP

(57) ABSTRACT

An ultrasonic transducer device is pressed against the front surface of a structure, emits an ultrasonic pulse into the structure, and detects an echo profile from the structure. An indicator is activated if the echo profile includes a return pulse that at least is received from between the front surface and the back surface of the structure. An ultrasonic transducer device includes an ultrasonic transducer and a coupling element coupled to the transducer for disposition between the transducer and a surface of a structure. The coupling element serves as a delay line that allows time for quiescence in the transducer so that return pulses from shallow depths can be detected. The ultrasonic transducer is activated when multiple switches are pressed against a surface thus assuring both firm coupling and perpendicular disposition of the acoustic axis of the transducer relative to the surface.

26 Claims, 6 Drawing Sheets

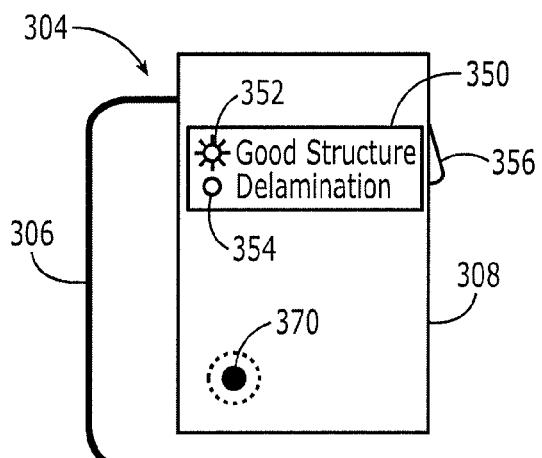
FIG. 2
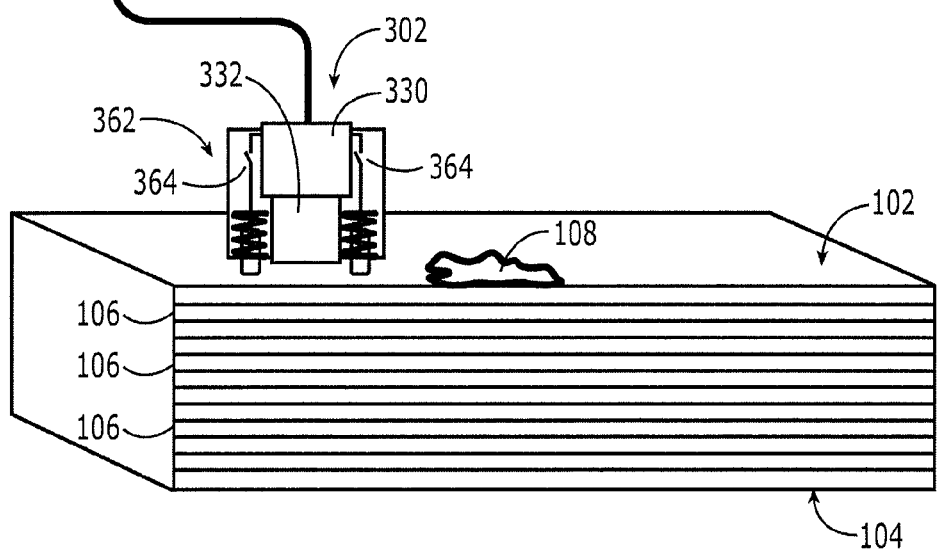
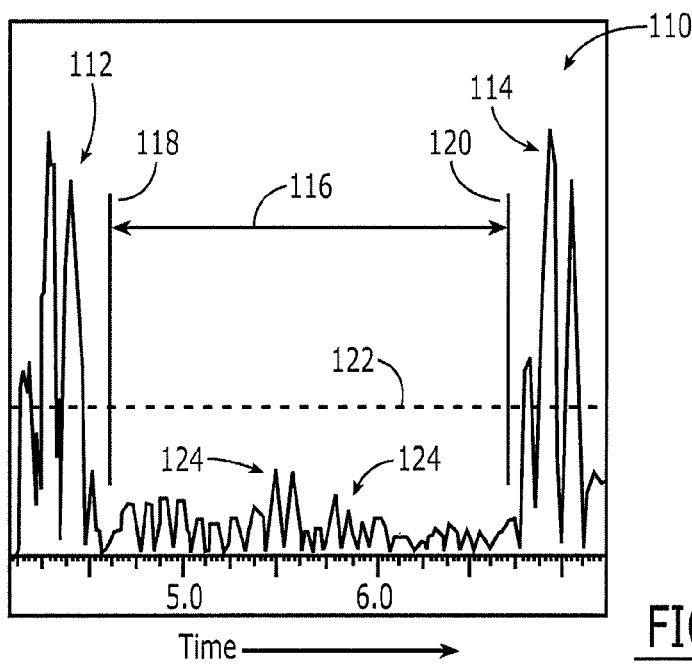
FIG. 3

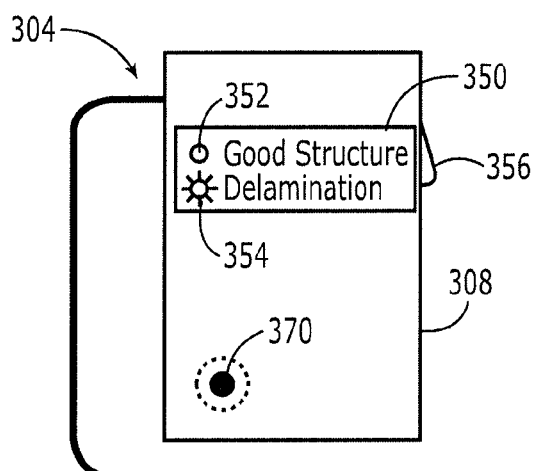
FIG. 4
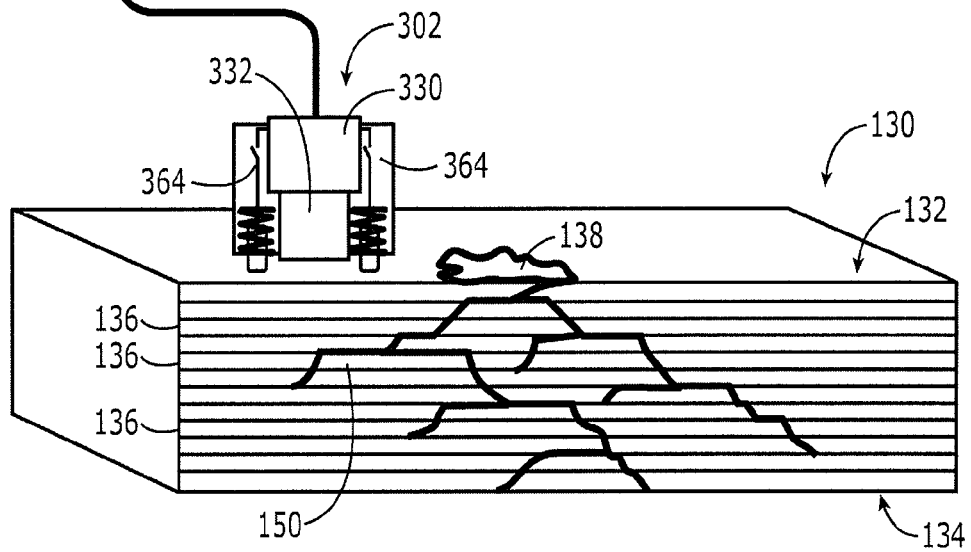
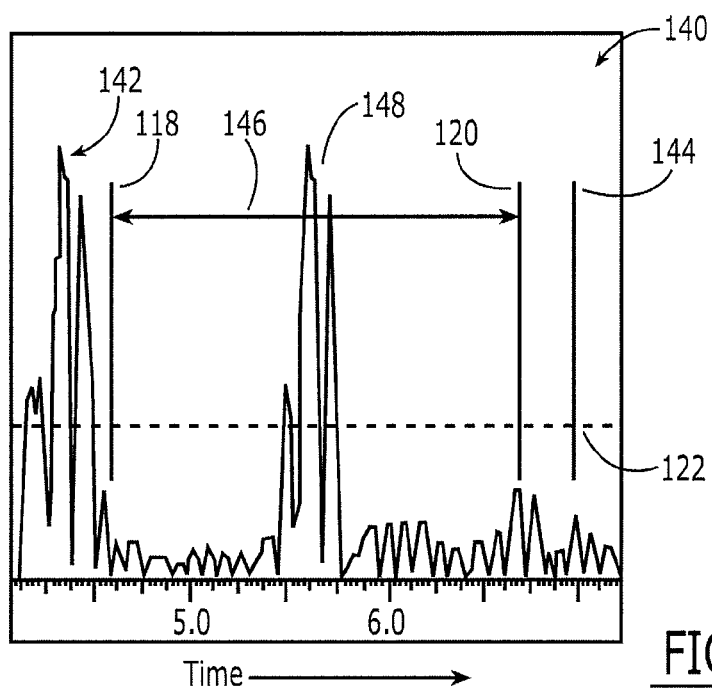
FIG. 5

CONVENIENT ULTRASONIC INSPECTION DEVICE

CROSS-REFERENCE TO RELATED APPLICATIONS

This application is a continuation-in-part, and claims the benefit of priority to, U.S. non-provisional patent application Ser. No. 10/870,962 of Kollgaard et al., filed Jun. 21, 2004, now U.S. Pat. No. 7,222,514 which co-pending patent application and the publication thereof, namely United States patent application publication Number US2005/0279171A1, published Dec. 22, 2005, are incorporated herein by reference.

FIELD OF THE INVENTION

Embodiments of the present invention relate generally to ultrasonic inspections of structures. More particularly, embodiments of the invention relate to devices and methods for non-destructive ultrasonic inspections of sub-surface portions of structures.

BACKGROUND OF THE INVENTION

Laminate composite materials are becoming increasingly common in the constructions of large aircraft. Typical laminate composite materials are composed of layered resin bonded graphite textiles. Like any material disposed along the exterior of an aircraft, laminate composite materials are subject to damages during the service life of an aircraft. In-flight collisions with birds and air-borne debris, and ground collisions involving loading and maintenance vehicles and equipment cause visible impact sites along the exterior of an aircraft. Assessments and repairs of laminate composite materials represent significant challenges with regard to efficiencies in time, cost, and training. Ground maintenance crews may be able to recognize impact sites along aircraft exteriors, but are typically not sufficiently trained or equipped to assess damages that may be associated with impact sites.

Damages in laminate composite materials tend toward morphologies with two important characteristics. In one characteristic, damages tend to initiate at impact sites and propagate into structures in expanding cone patterns. In another characteristic, deeper delaminations are rarely present without corresponding shallow delaminations. Therefore, at any impact site with delamination damage, shallow damage is likely to be present and can be construed as an indication that deeper damage is likely to exist. Unfortunately, visible impact sites that represent mere superficial markings are not easily distinguished by visual inspection from those overlying significant internal damages. Non-destructive inspection (NDI) devices are available so that inspections can reveal hidden sub-surface damages. For example, graphical representations such as ultrasonic C-scan images and infrared thermographic images can reveal sub-surface problems. However, typical available technologies require considerable training and experience. Thus, typical available NDI approaches are in the practice domains of highly trained specialists.

However, a typical scenario faced by commercial airlines occurs when a ground maintenance crew member spots an impact site along the exterior of an aircraft as the craft is serviced between flights. A decision must be made as to whether the aircraft should be permitted to fly or should be grounded for thorough inspections, damage assessments, and repairs if necessary. Consequences can be severe when such a decision is poorly made. Both safety and commercial viability must be preserved. Thus an aircraft with significant sub-surface damages along a wing or other structure should be grounded, and an aircraft having mere surface markings but no structural damages should be dispatched for flight. Trained NDI specialists and the equipment they may require are not typically immediately available at commercial aviation facilities. If specialists are to be summoned every time an impact site along the exterior of an aircraft is noticed, flight delays will occur, and passengers may need to be re-routed and possibly accommodated with hotel rooms and meals.

Thus, it would be advantageous to provide devices and methods for inspecting structures by modes requiring minimal training and interpretive expertise. Simplified methods in inspecting thin structures are needed. Methods are needed for detecting shallow damages in thicker structures, where shallow damages may indicate deeper damages. A need exists for rapid results providing go and no-go indications in NDI inspections.

BRIEF SUMMARY OF THE INVENTION

Embodiments of the invention may address at least some of the above needs and achieve other advantages. For example, a first aspect of the invention relates to a method of testing a structure having a front surface and a back surface. The method includes pressing an ultrasonic transducer device against the front surface of the structure, emitting an ultrasonic pulse into the structure, detecting an echo profile from the structure, and activating an indicator if the echo profile includes a return pulse that at least is received from between the front surface and the back surface. For example, an indicator may be activated if the echo profile includes a return pulse that at least occurs before an expected time of a return pulse from the back surface. Furthermore, an indicator may be automatically activated if the echo profile includes a return pulse that at least exhibits a time of flight of duration greater than a time of flight corresponding to the front surface, and less than a predetermined time of flight corresponding to a predetermined depth defined between the front surface and the back surface. An indicator that indicates no damage may be activated if the echo profile does not include a return pulse received from between the front surface and the predetermined depth.

Furthermore, at least one embodiment of the method of this first aspect includes automatically activating an indicator if the echo profile includes a return pulse that at least exhibits a time of flight of less duration than a predetermined time of flight corresponding to a predetermined depth defined between the front surface and the back surface, and an amplitude exceeding a predetermined threshold. Once an indicator is activated, additional ultrasonic pulses may be emitted, corresponding additional echo profiles may be detected, and an indicator may be continuously activated as long as detected echo profiles include return pulses that at least exhibit times of flight of less durations than the predetermined time of flight, and amplitudes exceeding the predetermined threshold.

At least one embodiment of the method of this first aspect includes pressing a coupling element coupled to an ultrasonic transducer into contact with the front surface. For example, the coupling element may include a material having a specific acoustic impedance that approximately matches the specific acoustic impedance of the structure under inspection. The coupling element may be constructed of an acoustic polymer and may be conveniently dry-coupled to a structure for interrogating the structure without a liquid couplant applied to the surface of the structure. Furthermore, in at least one embodiment of the inventive method, pressing an ultrasonic transducer device against the front surface of the structure includes pressing an activator attached to the ultrasonic transducer device against the front surface causing the ultrasonic transducer device to emit an ultrasonic pulse into the structure. Indeed, pressing an ultrasonic transducer device against the front surface of the structure may include simultaneously pressing multiple activators against the front surface. The multiple activators may partially surround an acoustic axis of the ultrasonic transducer device and simultaneously pressing the multiple activators may include directing the acoustic axis to be perpendicular to the front surface of the inspected structure. For determining whether damages have occurred in a structure near where an impact site is visible, an ultrasonic transducer device may be pressed against a front-surface portion near the impact site, and against multiple front-surface portions surrounding the impact site.

A second aspect of the invention relates to a diagnostic apparatus for detecting damages in a structure. The apparatus includes an ultrasonic transducer device, an indicator, and an electronic device. The ultrasonic transducer device is configured to be pressed against a structure having a front surface and a back surface, and is further configured to emit ultrasonic pulses into a structure and detecting echo profiles from the structure through the front surface. The electronic device is configured to activate the indicator if the ultrasonic transducer device detects an echo profile that includes a return pulse received from between the front surface and the back surface.

A third aspect of the invention relates to a diagnostic apparatus for inspecting a structure through a surface of the structure. The apparatus includes an ultrasonic transducer device configured to emit ultrasonic pulses and detect return pulses, an indicator, and an electronic device disposed in electronic communication with each of the ultrasonic transducer device and the indicator, the electronic device configured to automatically activate the indicator if the ultrasonic transducer device detects a return pulse that at least exhibits a time of flight of less duration than a predetermined time of flight. The diagnostic apparatus may include an activator assembly attached to the ultrasonic transducer device, the activator assembly configured to permit activation of the ultrasonic transducer device when the ultrasonic transducer device is pressed against a surface. For example, the diagnostic apparatus may include an activator assembly having multiple switches, which may surround an axis passing through the ultrasonic transducer device, configured to permit activation of the ultrasonic transducer device when all of the multiple switches are actuated simultaneously when the ultrasonic transducer device is pressed against a surface. In at least one embodiment of the ultrasonic transducer device of this first aspect includes an ultrasonic transducer and a coupling element coupled to the transducer for disposition between the transducer and a surface of a structure.

Furthermore, in at least one embodiment of the apparatus of this third aspect, the electronic device is configured to automatically activate the indicator if the ultrasonic transducer device detects a return pulse that at least exhibits a time of flight of duration greater than a first predetermined time of flight and less than a second predetermined time of flight. The ultrasonic transducer device may include an ultrasonic transducer and a coupling element for disposition between the transducer and a surface of a structure. The coupling element may have a proximal end coupled to the transducer and a distal end for pressing against a surface, and the first predetermined time of flight may correspond approximately to the distal end of the coupling element. The electronic device may be configured to automatically activate the indicator if the ultrasonic transducer device detects a return pulse that at least exhibits a time of flight of duration greater than a first predetermined time of flight and less than a second predetermined time of flight, and an amplitude exceeding a predetermined threshold. The electronic device may be configured to, once the indicator is activated, continuously activate the indicator as long as the ultrasonic transducer device detects return pulses that at least exhibit times of flight of durations greater than the first predetermined time of flight and less than the second predetermined time of flight, and amplitudes exceeding the predetermined threshold.

BRIEF DESCRIPTION OF THE SEVERAL VIEWS OF THE DRAWINGS

Figure 1:
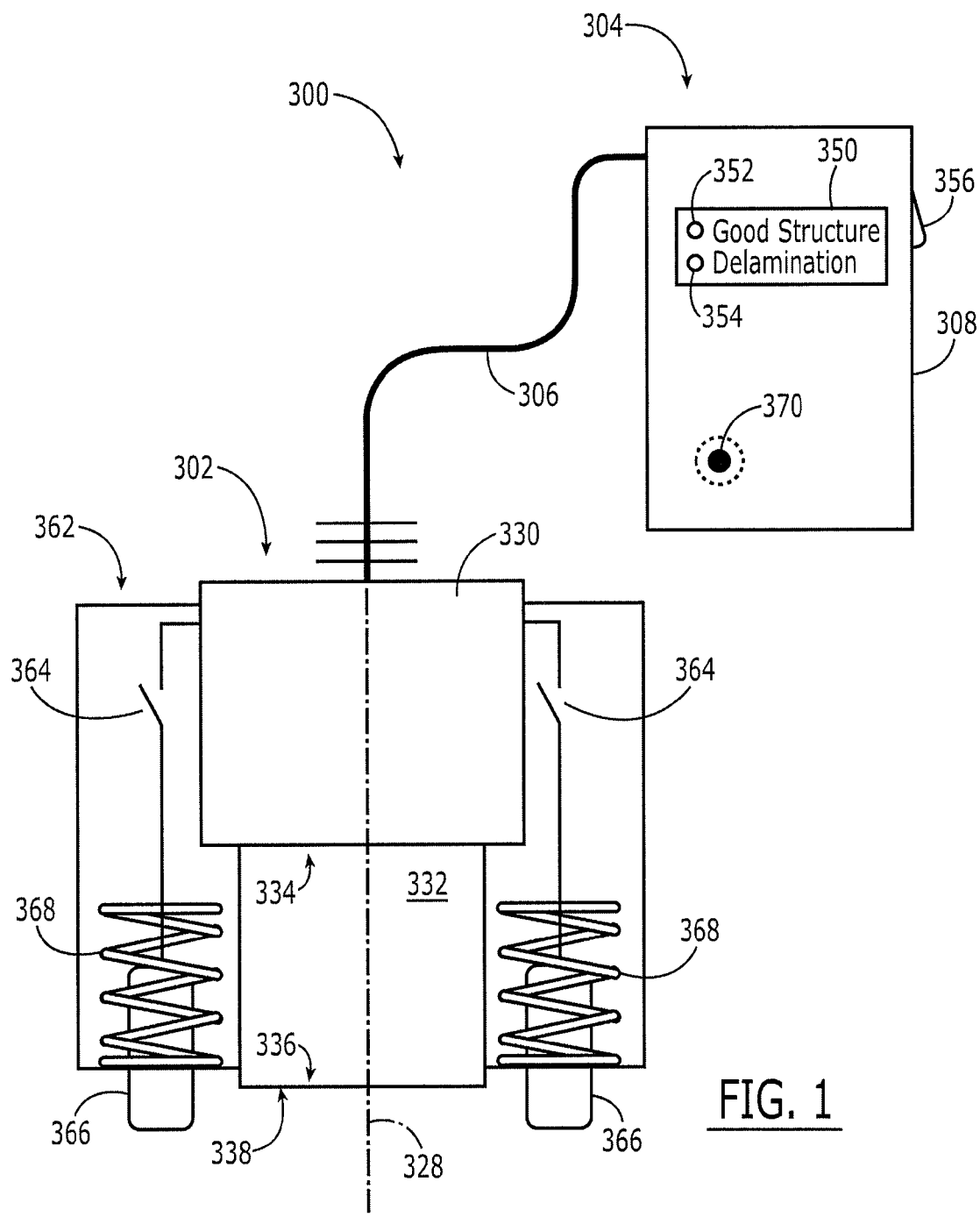
Figure 6:
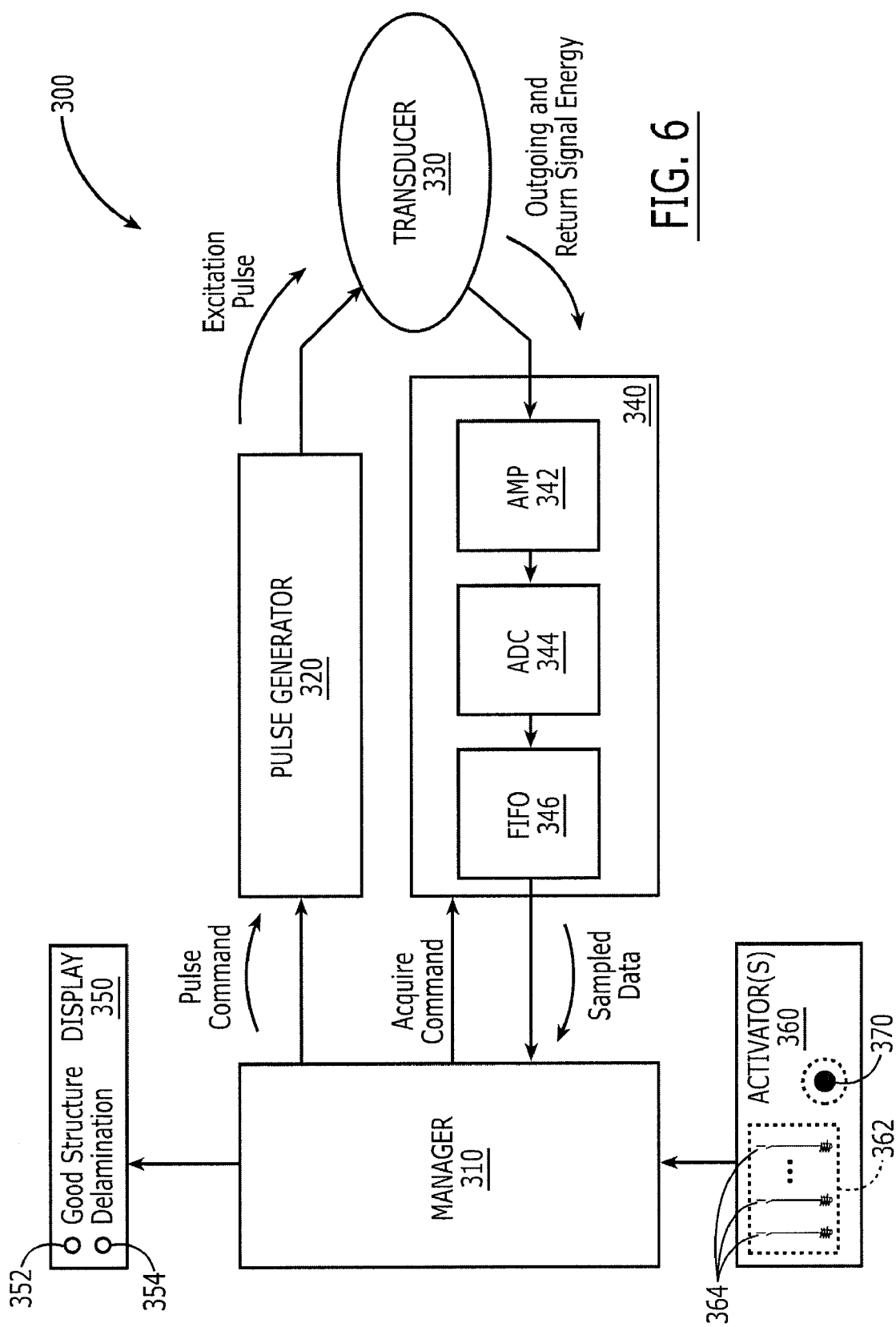
Figure 7:
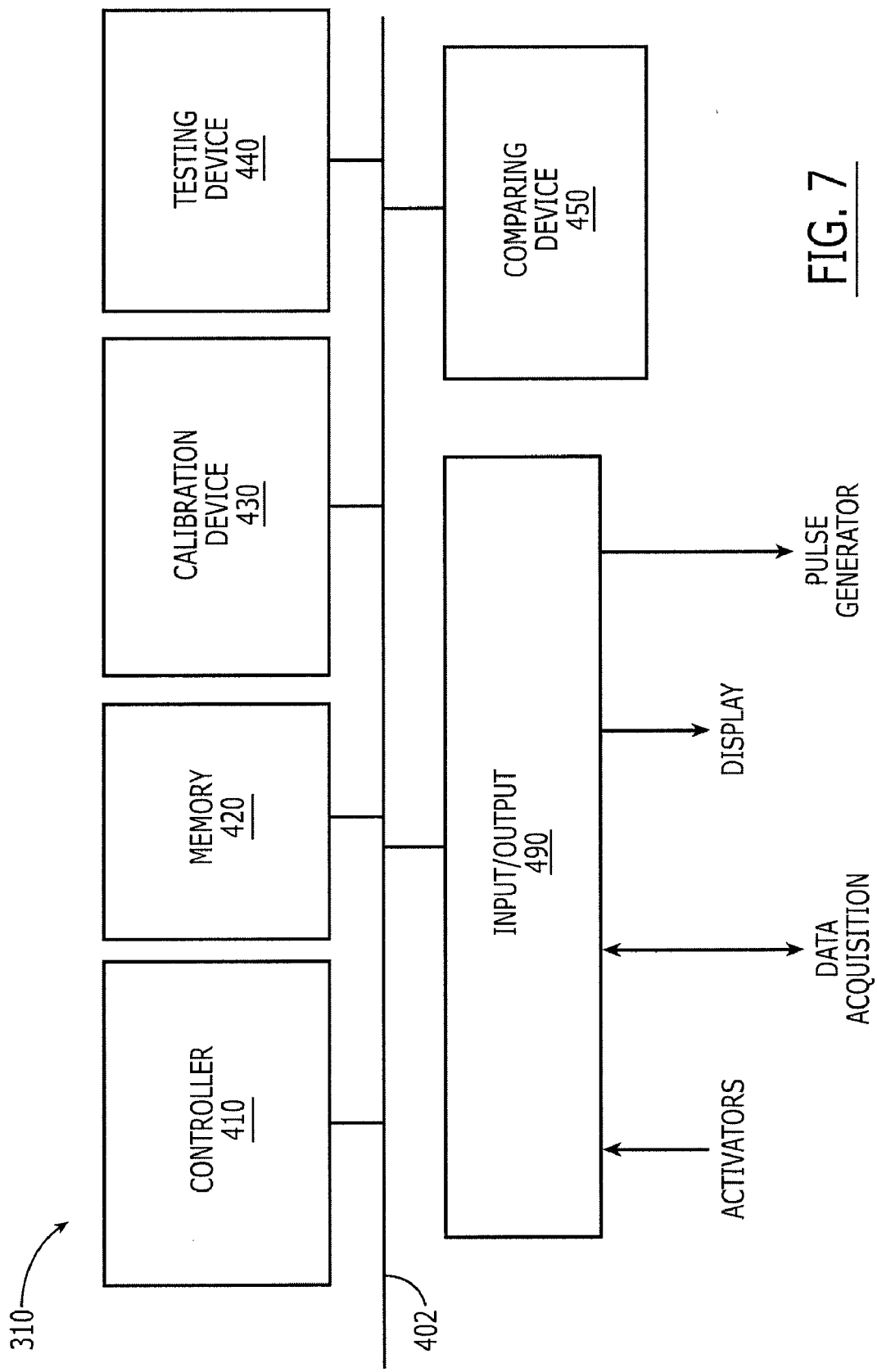
Figure 8:
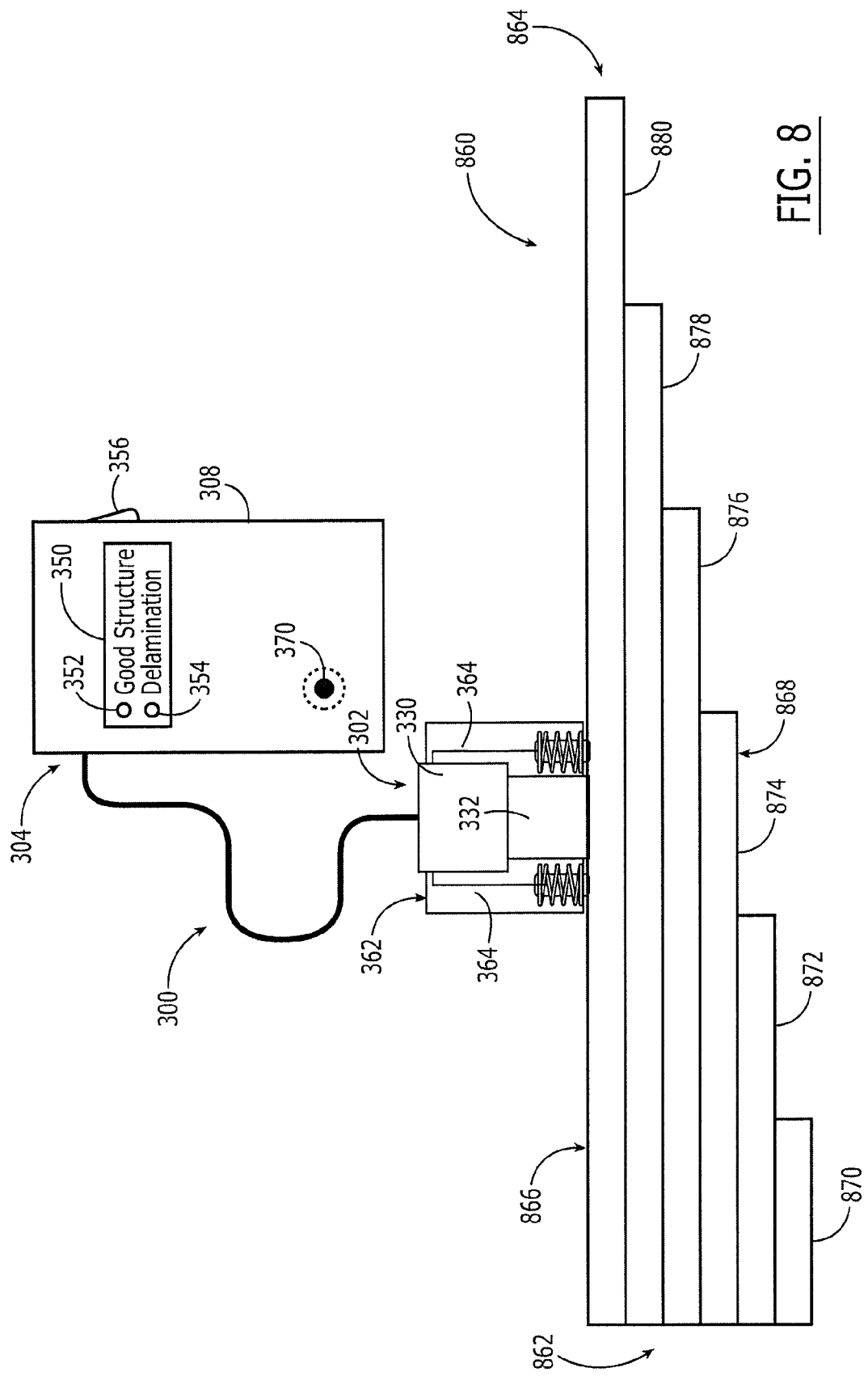

Having thus described the invention in general terms, reference will now be made to the accompanying drawings, which are not necessarily drawn to scale, and wherein:

FIG. 1 illustrates a diagnostic apparatus in accordance with one embodiment of the present invention, with an ultrasonic transducer device thereof shown in cross-sectional view;

FIG. 2 is a diagrammatic environmental view of the diagnostic apparatus of FIG. 1 shown inspecting a structure having no sub-surface flaws as indicated by a display of the apparatus;

FIG. 3 is a graph of an echo profile generated by the ultrasonic transducer device of FIG. 1 as disposed in FIG. 2;

FIG. 4 is diagrammatic environmental view of the diagnostic apparatus of FIG. 1 shown inspecting a structure having sub-surface flaws as indicated by the display of the apparatus;

FIG. 5 is a graph of an echo profile generated by the ultrasonic transducer device of FIG. 1 as disposed in FIG. 4;

FIG. 6 is a block diagram representing exemplary embodiments of electronic circuits of the diagnostic apparatus of FIG. 1;

FIG. 7 is a block diagram representing an exemplary embodiment of the manager of FIG. 6; and FIG. 8 is a diagrammatic environmental view of the diagnostic apparatus of FIG. 1 shown disposed along a calibration structure for calibration of the apparatus.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

FIG. 1 illustrates a diagnostic apparatus according to an embodiment of the present invention. The diagnostic apparatus 300 includes an ultrasonic transducer device 302 and an electronic device 304 having a housing 308, a display 350, a power switch 356, and a hidden calibration activator 370. The embodiment of the display 350 illustrated in FIG. 1 includes a first indicator 352 for indicating that no damages within an inspected structure are detected by the apparatus, and a second indicator 354 for indicating that damages may be present. The ultrasonic transducer device includes an ultrasonic transducer 330 and a coupling element 332 coupled to the transducer for disposition between the transducer and a surface of a structure under inspection. An activator assembly 362 is attached to the ultrasonic transducer device 302. As will be described in the following in further detail, when the apparatus is used to inspect a structure, the ultrasonic transducer device 302 is pressed against a surface of the structure and one of the first and second indicators is automatically activated to indicate whether, respectively, the structure is likely in good condition or that damages may be present in the structure. The diagnostic apparatus is thus useful to operators who may not be highly trained in sophisticated NDI visualization technologies. For example, a ground maintenance crew member at an aviation facility could use the apparatus to rapidly determine whether concerns about a visible impact site on an inspected aircraft structure can be dismissed or if the services of inspection specialists should be solicited.

The ultrasonic transducer 330 is operable as a pulse-echo inspection sensor that both sends and receives ultrasonic waves. Such transducers are commercially available and can be fabricated, for example, from a polymer-based piezo-electric material called polyvinylidene fluoride (PVDF). The ultrasonic transducer 330 typically sends an ultrasonic pulse into an inspected structure and then generates an electrical signal when an ultrasonic echo signal returns from the structure. Outgoing ultrasonic pulses traveling through a structure tend to reflect from surfaces, edges, and other discontinuities such as damages in the structure. A returning ultrasonic echo signal can include multiple time-distributed return pulses and thus returning ultrasonic echo signals are referred to herein as echo profiles. Typical echo profiles include return pulses reflected from surfaces and edges that are expected and from damages that deserve investigation and repair. The electrical signal generated by the ultrasonic transducer conveys amplitude and time data corresponding to the amplitudes and arrival times of return pulses within the echo profile. The electronic device 304 activates the ultrasonic transducer 330 to send outgoing ultrasonic pulses and receives signals generated by the transducer by way of one or more conductive cables 306, which can have a length as desired for holding and moving the ultrasonic transducer device 302 separately from the electronic device 304.

The ultrasonic transducer 330 defines an acoustic axis 328, or maximum response axis, along which outgoing pulses are maximally directed and along which the transducer has maximum sensitivity for detecting returning echo profiles. A coupling element 332 having a proximal end 334 coupled to the transducer 330 and an opposing distal end 336 is disposed about the acoustic axis 328 for, among other things, coupling the transducer to a structure when a structure is to be inspected. The distal end 336 defines a generally planar contact surface 338, which is perpendicular to the acoustic axis 328, for pressing against the surface of an inspected structure. The coupling element is generally constructed of deformable and rubbery acoustic polymer material. The ultrasonic transducer device 302 may be a dedicated device intended toward inspecting a particular type of structural material. In that context, the coupling element may be acoustic-impedance matched with the particular type of structure material. That is, the coupling element may be constructed of a selected acoustic polymer material having a specific acoustic impedance that approximately matches the specific acoustic impedance of the particular type of structure material. Such impedance matching promotes the transfer of acoustic energy across the junction of the contact surface 338 and the surface of an inspected structure, minimizes reflections at the junction, and thus promotes the sensitivity of the ultrasonic transducer device. Acoustic polymers having various specific acoustic impedance values are known and are commercially available for impedance matching purposes.

The activator assembly 362 includes multiple switches 364 that permit activation of the ultrasonic transducer 330 when all of the multiple switches are simultaneously actuated. The power switch 356, when opened, prevents accidental activation of the ultrasonic transducer when the switches are inadvertently pressed such as when the device 302 is carried and stored. Each switch 364 includes a respective contact member 366 biased by a respective spring 368 toward a disposition in which the switch is open. Each switch closes when the respective contact member is pressed against the surface of a structure under inspection. The contact members are preferably constructed of a material that is durable yet is unlikely to damage an inspected structure. For example, the contact members can be constructed of polytetrafluoroethylene (PTFE), which is available from Dupont™ as Teflon®. The multiple switches 364 together surround the acoustic axis 328 of the ultrasonic transducer 330. The switches are all simultaneously closed, or actuated, when the ultrasonic transducer device is pressed against a surface such that the contact surface 338 of the coupling element 332 is pressed against, and disposed perpendicular to, the surface of an inspected structure. Thus, the activator assembly 362 provides a convenient triggering advantage, a coupling assurance advantage, and an alignment advantage. The electronic device 304 is prompted to activate the ultrasonic transducer 330 upon simultaneous actuation of all of the multiple switches, which essentially requires both that the acoustic axis 328 of the transducer 330 is directed perpendicular to the surface of a structure under inspection and that the contact surface 338 of the coupling element firmly contacts the surface of the structure.

The diagnostic apparatus 300 is shown in FIG. 2 inspecting a structure 100. The ultrasonic transducer device 302 is shown pressed against a front surface 102 of the structure such that all of the multiple switches of the activator assembly 362 are actuated. The ultrasonic transducer 330 thus emits one or more ultrasonic pulses into the structure and detects the echo profile 110 shown in FIG. 3. The apparatus 300 is disposed along the surface 102 at a surface location where no flaws are present in the structure. Thus, the echo profile 110 detected by the apparatus is characteristic of a good structure.

FIG. 2 depicts an exemplary laminate structure 100 capable of being used on any number of structures, such as those found on airplanes, automobiles and other vehicles, or any other structure that can benefit from a light, yet strong material. The laminate structure 100 has a front-surface 102 and a back-surface 104 and is composed of multiple individual laminate sheets 106. The laminate sheets are joined together by a bonding material.

The exemplary laminate sheets 106 are composed of sheets of graphite fibers joined by a bonding material composed of an ester based resin. However, it should be appreciated that these descriptions relate to sheets constructed of other materials. Such other materials include, but are not limited to: carbon-based fabrics; metal foils; and polymer-based fabrics such as Kevlar®. Furthermore, while the laminate structure 100 of FIG. 2 is formed using an ester-based resin, these descriptions relate as well to other bonding materials.

In the course of normal use, laminate materials are subject to accidental damages. For example, where laminate materials are used to cover the front surfaces of aircraft wings, impact damages from birds and airborne debris can occur with every flight. In some instances the resultant damage will be very light while in other instances the damage may be moderate to severe. For example, the laminate structure 100 in FIG. 2 is depicted as being so lightly damaged that a marking visibly apparent at an impact site 108 is merely superficial and represents no threat to the integrity of the structure.

The electrical waveform 110 shown in FIG. 3 represents the electrical signal generated by the ultrasonic transducer 330 as graphically displayed on an instrument such as an oscilloscope. Electrical fluctuations having various amplitudes rise vertically above the "Time" axis such that early fluctuation events are shown on the left and later subsequent ordered events occurring in time are represented by considering the waveform from left to right. Thus the electrical fluctuation group 112 is generated by the ultrasonic transducer 330 before the electrical fluctuation group 114. The fluctuation groups 112 and 114 have respective amplitudes that are greater than those of the minor fluctuations 124. Though the fluctuation groups 112 and 114 are composed of high-frequency oscillations, such groups will be referred to herein as "pulses." Furthermore, the electrical waveform 110 is appreciated by those skilled in the arts of ultrasonic measurements and NDI technologies as representing multiple time-ordered ultrasonic return pulses that echo from features of an ultrasonically inspected structure. Thus, waveforms such as the electrical waveform 100 will be referred to herein as "echo profiles," and the electrical pulses such as the pulses 112 and 114 will be referred to herein as "return pulses."

The echo profile 110 includes the return pulse 112 that returned from the front surface 102 of the structure 100 as an echo after an outgoing ultrasonic pulse was sent toward the structure, through the coupling element 332, by the ultrasonic transducer 330. The echo profile also includes the return pulse 114 that similarly returned as an echo from the back surface 104. Outgoing pulses are not illustrated as portions of echo profiles herein but should be understood to have occurred at times preceding the front-surface return pulses in FIGS. 3 and 5. Outgoing pulses are illustrated in time relations to return pulses in the U.S. Patent Application Publication US2005/0279171A1, which is a published version of the U.S. patent application Ser. No. 10/870,962 of Kollgaard et al., and which is incorporated herein in its entirety by this reference.

In the identified patent application publication, however, return pulses from front surfaces of inspected structures are not illustrated. Some embodiments of the present invention include an acoustic coupling element disposed between an ultrasonic transducer and a front surface of an inspected structure. Such a coupling element serves to provide dry coupling between the transducer and an interrogated structure and serves as a delay line in that it imposes a delay time between outgoing pulses at the transducer and return pulses according to the length of the coupling element and according to the speed of ultrasonic pulse transmissions within the coupling element. If an ultrasonic transducer is coupled to a surface without a delay line, an outgoing pulse, or "main bang" as such pulses are sometimes called, is closely followed by a return pulse from the surface. In such a situation, the outgoing pulse and the front-surface return pulse are difficult, and may be impossible, to separately distinguish and illustrate.

However, the coupling element 332 in FIG. 2 spaces the ultrasonic transducer 330 from the front surface 102 of the structure under inspection. Thus, the time of flight (TOF) of the front-surface return pulse 112 includes at least the time required for an outgoing pulse to propagate from the transducer, to the contact face 338 (FIG. 1) of the coupling element, and back to the transducer. Thus, the outgoing pulse would have occurred prior to the time range depicted in FIG. 3. It should be understood that, in this context, the TOF of a return pulse is generally defined as the time elapsed between the time of a transducer's sending of an outgoing pulse and the time of the transducer's receipt of the return pulse. Thus, the "Time" axis of FIG. 3 can be considered a portion of a relative TOF axis, wherein the origin of the axis, as defined by the time of an outgoing pulse, is not shown.

A time-gated portion 116 of the echo profile is disposed between a gate-initiating time 118 and a gate-closing time 120. The initiating and closing times are predetermined according to a calibrating procedure such as that discussed in the following with reference to FIGS. 6-8. Ultrasonic waves tend to echo from structural discontinuities such as surfaces and flaws including delaminations, fissures, voids, and contaminants. In FIG. 3, the time-gated portion 116 of the echo profile is free of significant return pulses because such flaws are not present in the structure 100 in FIG. 2. More particularly, such flaws are not present in the structure under the ultrasonic transducer device 302. In order for the diagnostic apparatus 300 to distinguish significant return pulses that reveal the presence of structural flaws from insignificant noise and minor fluctuations 124, a threshold 122 may also be predetermined or established according to a calibrating procedure such as that discussed in the following with reference to FIGS. 6-8. In FIG. 3, no return pluses having amplitudes exceeding the threshold 122 are within the time-gated portion 116 of the echo profile 110. According to the configuration and calibration of the electronic device 304, the indicator 352 is automatically activated to indicate no damages are detected when the ultrasonic transducer device 320 is pressed against the front surface of a structure and the echo profile detected from the structure does not include a return pulse within the time gate defined between the initiating and closing times 118 and 120. Thus, due to quiescence, relative to the threshold 122, within the time-gated portion 116 of the echo profile 110 in FIG. 3, the indicator 352 is activated in FIG. 2 though minor fluctuations 124 having amplitudes below the threshold 122 are present within the time-gated portion.

In FIG. 4, the diagnostic apparatus 300 inspects a laminate structure 130 wherein flaws such as delaminations reside. In this figure, the impact site 138 is disposed above a damaged region of the structure. The damage likely began at the impact site along the front surface 132 of the structure and propagated toward the back surface 134 in an expanding cone pattern as illustrated. Such cone patterns are typical in damaged laminate structures as damages can extend both deeply into a structure and laterally around an impact site. Thus, when an impact site is observed on a surface, it is good practice to inspect a structure for hidden damages residing below surface portions that surround the impact site. In FIG. 4, the ultrasonic transducer device is pressed against a front surface portion near the impact site. An echo profile 140 detected by the device is shown in FIG. 5. In this echo profile, a front-surface return pulse 142 is detected but no significant back-surface return pulse is detected. However, a return pulse 148 is received and detected from between the front surface and the back surface. Apparently, the energy of outgoing pulses from the ultrasonic transducer device are spent, at least in part, by the hidden damages 150 in FIG. 4, without significant return pulses being received from the back surface 134. Nonetheless, the return pulse 148 occurs before an expected time 144 of a return pulse from the back surface, without regard to whether a back-surface return pulse is actually received. That back-surface return pulses can be affected by intervening damages is discussed in the incorporated U.S. Patent Application Publication US2005/0279171A1.

The time-gated portion 146 of the echo profile 140 of FIG. 5 is established similarly as the time-gated portion 116 of the echo profile 110 of FIG. 3. That is, the gate-initiating times 118 are essentially identical in FIGS. 3 and 5, as are the gate-closing times 120. Additionally, the thresholds 122 in FIGS. 3 and 5 are essentially identical as well. Thus, the calibration of the diagnostic apparatus 300 is maintained across the scenarios illustrated in FIGS. 2-5. According to the configuration and calibration of the electronic device 304, the indicator 354 is automatically activated to indicate that a delamination flaw may be detected when the ultrasonic transducer device 320 is pressed against the front surface of a structure and the echo profile detected from the structure includes a return pulse within the time gate between the initiating and closing times 118 and 120. Thus, due to the presence of the return pulse 148 (FIG. 5) within the time gate, which pulse has a magnitude exceeding the threshold 122, the indicator 354 is activated in FIG. 4 to alert an operator to the likely presence of hidden damages in the structure.

The time-gate initiating and closing times 118 and 120 are established by choice to closely follow and precede front-surface and back-surface return pulses. This configuration choice for the diagnostic apparatus 300 serves to detect return pulses, within an echo profile, received from between the front and back surfaces. However, depth is correlated with the time of flight (TOF) measured between the dispatch of an outgoing pulse and the receipt of a return pulse. Once a time gate is established, relative quiescence and relative return-pulse activity, with respect to the established threshold, within the time gate cause automatic activations of the indicators 352 and 354, respectively. This is true without regard to the ongoing presence of front and back surface return pulses. Thus, in a more general sense, the initiating and closing times can be established so that the diagnostic apparatus informs an operator of the likely presence or absence of return pulses from any chosen depth range. Any desired depth range, defined between a first depth and a second depth, can be chosen for inspection by establishing or predetermining both a gate-initiating time corresponding to the first depth, and a gate-closing time corresponding to the second depth.

FIG. 6 is a block diagram representing exemplary embodiments of electronic circuits and connections of the diagnostic apparatus 300. As shown in FIG. 6, the diagnostic apparatus 300 includes a manager 310, a pulse generator 320, the transducer 330, a data acquisition device 340, the display 350 represented to include at least the indicators 352 and 354 (FIG. 1), and a number of activators 360 represented to include at least the multiple switches 364 of the activator assembly 362 and a calibration activator 370. FIG. 6 represents the circuits and connections without particular regard to physical arrangements of circuit components. Thus, while other arrangements are well within the scope of these descriptions of FIG. 6, the ultrasonic transducer device 302 of FIG. 1, to which the activator assembly 362 is attached, includes the transducer 330, while the electronic device 304 of FIG. 1 includes the display 350, the calibration activator 370, the manager 310, the pulse generator 320, and the data acquisition device 340.

The data acquisition device 340 includes an amplifier (AMP) 342, an analog to digital converter (ADC) 344 and a first-end-first-out buffer (FIFO) 346. While the diagnostic apparatus 300 is represented to include a collection of various integrated circuits and other components coupled together on a single circuit-board, it should be appreciated that, the diagnostic apparatus 300 can take other forms. For example, in various embodiments, the pulse generator 320, as well as the FIFO 346 and ADC 344 may be incorporated into a bussed structure such as that commonly used on many processor-based systems. In still other embodiments, it should be appreciated that many of the illustrated components may be incorporated on a single integrated circuit, with the understanding that the display, transducer, and activators might be located off-chip.

For the exemplary electronic circuits and connections of FIG. 6, there are at least two modes of operation: a calibration mode for executing calibration cycles to calibrate the diagnostic apparatus 300; and a test mode for executing test cycles to use the apparatus to inspect a structure. Execution of the calibration mode of the diagnostic apparatus 300 entails calibrating the apparatus against a calibration structure in a relatively simple, time-efficient, and cost-effective procedure. In comparison, calibration procedures for other types of inspection devices can require that technicians spend hours characterizing the various components within the devices. It is expected that the diagnostic apparatus 300 may be calibrated by trained NDI specialists, who may be stationed at particular NDI and equipment calibration facilities. The calibrated diagnostic apparatus may then be distributed for use, for example, by maintenance crews at aviation facilities.

To start a calibration cycle, an operator initially presses the transducer device 302 against a calibration structure, causing simultaneous actuations of all of the switches 364 (FIG. 1) of the activator assembly 362. The operator additionally actuates the calibration activator 370, which can be, for example, a hidden or locked switch. For example, the calibration activator may be disposed within the housing 308 of the electronic device 304 (FIG. 1) and hidden from typical maintenance crew operators so that only NDI specialists typically actuate the calibration activator. Alternatively, the calibration activator may be recessed but available along the exterior of the housing for actuation by a stylus in order to prevent inadvertent actuation, which could cause a loss of established calibration.

Actuations of the switches 364 permit activation of the ultrasonic transducer 330, and actuation of the calibration activator 370 provides the manager 310 with an indication that a calibration cycle is desired. In response to these actuations, the manager 310, will generate a command signal to the pulse generator 320. The pulse generator 320, in turn, receives the command signal from manager 310 and sends an excitation pulse having a particular amplitude and duration to the transducer 330. The transducer 330 receives the excitation pulse and emits a burst of ultrasonic energy, referred to herein as an outgoing pulse or main bang.

In the exemplary diagnostic apparatus 300 of FIG. 6, the pulse generator 320 can accept a TTL-compatible command signal, such as a low-to-high transition, and generate an excitation pulse having an amplitude of about 25-30 volts and a duration of about 200 nanoseconds. However, it should be appreciated that other types of command signals and excitation pulses are within the scope of these descriptions.

The transducer 330 generally both sends outgoing pulses and detects echo profiles returning to the transducer. The transducer 330 transforms echo profiles of ultrasonic energy into electrical analog signals that are received by the data acquisition device 340. Signals received by the data acquisition device 340 are passed to the amplifier 342 which can buffer, amplify and filter the electric analog signals which then pass to the ADC 344. The ADC 344 converts analog electrical signals to digital data. Subsequently, the digital data is passed to FIFO 346, where it can be stored until extracted by the manager 310.

FIG. 7 is a block diagram of an exemplary embodiment of the manager 310 of FIG. 6. As shown in FIG. 7, the manager 310 includes a controller 410, a memory 420, a calibration device 430, a testing device 440, a comparing device 450 and an input/output port 490. The various components of the manager 310 are coupled together by way of a data/address bus 402. While the exemplary manager 310 is depicted as a device having a bussed architecture with various peripherals, it should be appreciated that in other embodiments, the manager 310 can appear as a single-chip processor with integrated components, a general purpose processor, a digital signal processor, a programmable logic chip (PLC) executing software, or any other system capable of executing a series of instructions from a memory. Furthermore, it should be appreciated that the manager 310 can take the form of any number of discrete logic circuits capable of performing the various required functions as described herein. Still further, it should be appreciated that, in various other embodiments, components of the manager 310, such as the calibration device 430, the testing device 440, and the comparing device 450 can take the form of various programs and routines embedded in memory 420.

After data acquisition has started, the manager 310 extracts information from the FIFO 346 (FIG. 6), and stores the information in a local memory 420 for use in a test cycle. In particular, the manager is configured to determine at least the TOF of back-surface return pulses detected during calibration cycles. The manager identifies the pulse having the greatest amplitude following the expected TOF of a front-surface return pulse. In so far as the ultrasonic transducer device 302 is pressed against the surface of a good structure when a calibration cycle is initiated, only back-surface return pulses should follow front-surface return pulses and exceed the established threshold 122 as shown in FIG. 3. The threshold may be established as a parameter within software executed by the manager. A test point may be available within the housing, for example upstream or downstream of the amplifier 342, so that a calibration specialist can sample and view echo profiles such as that shown in FIG. 3 to confirm the programming of the manager and the performance of the diagnostic apparatus 300. The manager may automatically set the gate-closing time 120 (FIG. 3) to precede the TOF of the identified back-surface return pulse. For example, the manager may subtract a fixed or adjustable time decrement from the TOF of back-surface return pulses to establish the gate-closing time.

The expected TOF of a front-surface return pulse may be a permanent parameter, an adjustable parameter, or may be automatically determined by the manager 310. The expected TOF of a front-surface return pulse corresponds approximately to the time elapsed as an ultrasonic pulse twice traverses the length of the coupling element as measured between the proximal and distal ends 334 and 336 thereof. Thus, in embodiments of the ultrasonic transducer device 302 wherein the coupling element 332 is a fixed component, the TOF of an ultrasonic pulse that travels from the proximal end to the distal end, and back again, may be a fixed time interval and thus may be a permanent parameter. Alternatively, a front-surface return pulse may be identified by the manager 310 as the earliest return pulse that exceeds a threshold. Thus, the TOF of a front-surface return pulse may be automatically determined. Whether the expected TOF of a front-surface return pulse is a permanent parameter or is automatically determined, an adjustment device may be hidden within the housing 308 of the electronic device 304 so that a calibration specialist can make adjustments affecting the parameter or determination.

The gate-initiating time 118 (FIG. 3) typically closely follows the expected TOF of a front-surface return pulse so that the diagnostic apparatus is calibrated to be sensitive to shallow flaws such as delaminations disposed in an inspected structure near the front surface. The manager may automatically set the gate-initiating time 118 (FIG. 3) to follow the TOF of front-surface return pulses. For example, the manager may add a fixed or adjustable time increment to the TOF of front-surface return pulses to establish the gate-initiating time. For example, such a time increment may be established as a parameter within software executed by the manager.

The manager 310 generally coordinates a calibration cycle once the calibration activator is actuated, and the ultrasonic transducer device is pressed against a surface. In response, the manager 310 issues a command signal to the pulse generator 320 shown in FIG. 6, as well as a capture signal to the data acquisition device 340. The controller 410 subsequently imports captured calibration-cycle data by way of the input/output port 490, and stores the captured data in the memory 420. The controller 410 then moves the captured calibration-cycle data from the memory 420 to the calibration device 430. As the calibration device 430 receives the calibration-cycle data, it performs operations to identify return pulses and to determine the amplitudes and times-of-flight of return pulses. Furthermore, the calibration device may characterize pulse shape information, and phase information. During calibration cycles, the calibration device 430 typically at least detects back-surface return pulses which may exhibit distortions and noise contaminations that can be abated or compensated by the calibration device.

Return pulses may be corrupted by excessive noise and return-pulses may be caused by unexpected defects. The calibration device 430 is configured to recognize that received data is problematic and subsequently issue an indication that a problem with the calibration cycle has occurred. Assuming that a calibration specialist receives such an indication, the specialist can perform a second calibration cycle on another portion of the subject laminate structure until a good calibration cycle is performed and valid calibration is established. Furthermore, the manager 310 may coordinate a single calibration cycle wherein a single outgoing pulse is sent and a corresponding echo profile is detected, or the manager 310 may coordinate a plurality of calibration cycles and utilize statistical processing to determine calibration parameters such as gate-initiating and gate-closing times.

Once calibration of the diagnostic apparatus is established, the apparatus can be distributed to an operator such as a member of a maintenance crew at an aviation facility. An operator can then press the ultrasonic transducer device 302 against a surface of a structure in order to detect delaminations and other flaws disposed within the structure between the depths respectively corresponding to the established gate-initiating and closing times. Assuming the power switch 356 (FIG. 2) is closed, simultaneous actuations of all of the multiple switches 364 causes the initiation of a test cycle. As with the calibration mode, the manager 310 sends a command signal to the pulse generator 320, which in turn sends an excitation pulse to the transducer 330. The transducer emits an outgoing ultrasonic pulse, detects return pulses, and generates an electrical signal which conveys echo profile information to the data acquisition device 340.

The controller 410 subsequently imports captured test-cycle data by way of the input/output port 490, and stores the captured data in the memory 420. The controller 410 then moves the captured test-cycle data from the memory 420 to the testing device 440. As the testing device 440 receives the test-cycle data, it performs operations to identify return pulses and to determine the amplitudes and times-of-flight of return pulses. The comparing device 450 receives return-pulse amplitude and TOF data from the testing device and determines whether any return pulses exceeding the established threshold are present within the established time gate defined between the gate-initiating and gate-closing times 118 and 120 (FIG. 5). If the comparing device 450 determines such a return pulse is present, the manager activates the first indicator 352. If the manager determines no such return pulse is present, the manager activates the second indicator 354. The manager 310 may coordinate a single test cycle wherein a single outgoing pulse is sent and a corresponding echo profile is detected, or the manager 310 may coordinate a plurality of test cycles and utilize statistical processing to determine whether any return pulses exceeding the established threshold are present within the established time gate.

The first and second indicators 352 and 354 may each be, for example, a respective light source such as a respective light-emitting diode (LED). They may emit respective different colors when activated. For example, the first indicator may be an LED that emits green light, and the second indicator may be an LED that emits red light. Furthermore, the indicators may be other types of light sources. Moreover, the indicators may comprise other types of light sources and may comprise sound sources. By first and second indicators, these descriptions may relate to differing aspects of a single indicator. For example, activating the first indicator may entail light of a first color from an emitter, and activating the second indicator may entail light of a second color from the same emitter. The indicators can also be separate regions of an LCD device. The manager may include a dwelling functionality to prevent rapid cycling between activations of the first and second indicators, for example when a return pulse present in a time gate closely reaches the threshold.

With further regard to the calibration of the diagnostic apparatus 300, a calibration cycle can be initiated with the ultrasonic transducer device 302 pressed against a good portion of a structure, as shown in FIG. 2, in order to prepare for testing other portions of the structure. However, the assurance of the calibration of the diagnostic apparatus following such a calibration procedure may be as questionable as any assumption that a good portion of a structure was interrogated. Thus, a calibration structure can be provided in order to assure that calibration is completed on a well characterized material sample. An exemplary stepped wedge calibration structure 860 is illustrated in FIG. 8. The calibration structure is illustrated as a sample of layered laminate material. Preferably, the material of the calibration structure matches or is closely similar to the material for which the diagnostic apparatus 300 is to be calibrated to inspect. The calibration structure has progressively lesser depths along stages or steps proceeding from a first end 862 to a second end 864. As shown, the ultrasonic transducer device 302 can be disposed against any selected stage of the calibration structure in order to calibrate the apparatus 300 toward inspections of any depth range available among the stages. The stepped wedge calibration structure 860 can also be used to confirm the calibration and performance of the apparatus. For example, once the apparatus is calibrated to detect flaws such as delaminations at depths between the front surface 866 of the calibration structure and the back surface 868 of the third stage 874, good structures should be indicated by the first indicator 352 when the transducer device 302 is pressed against the front surface along the first and second stages 870 and 872, which are deeper than the third stage 874. On the other hand, in this example, delaminations should be indicated by the second indicator 354 when the transducer device 302 is pressed against the front surface along the fourth, fifth, and sixth stages 876, 878, and 880, which are shallow when compared to the third stage 874.

A particular advantage of the diagnostic apparatus 300 resides in the ability of the apparatus 300 to inspect a structure in a depth range including shallow portions of a structure. The gate initiating time can be established to correspond to a depth just below the surface of a structure. The delay-line aspect of the coupling element 332 allows time for quiescence, following outgoing main-bang pulses, to occur in the transducer 330 before return pulses are received from shallow depths. NDI devices having no delay lines are typically blind to shallow-depth return pulses because the main bang interferes with front surface return pulses when a transducer is placed in direct or near contact with a structure.

Another particular advantage of the diagnostic apparatus 300 resides in its insensitivity to back surface conditions once a time gate is established. The diagnostic apparatus 300, once calibrated, inspects a structure in an established or predetermined depth range without further regard to the ongoing presence or magnitudes of back-surface return pulses. Thus, the apparatus can be calibrated to inspect a depth range of a skin of an aircraft or other construction and then moved about on the skin without regard to back-surface conditions. In that context, the presence of structural stiffeners or other components bonded to the back surface of the skin have essentially no effect on the performance of the apparatus.

Yet another advantage of the diagnostic apparatus 300 resides in the simplicity of its indicators 352 and 354. These, in a sense, respectively provide go and no-go test results. The diagnostic apparatus 300 can be calibrated by a trained NDI specialist and distributed to aviation facility maintenance crews. An operator without sophisticated training in NDI techniques need not be confounded by A-scan (waveform), B-scan (profile), and C-scan (mapping) displays. Such an operator can be informed, however, of whether or not significant damages likely reside in an inspected structure. If the "Good Structure" indicator 352 is activated, an inspected structure can be dispatched for use. On the other hand, if the "Delamination" indicator 354 is activated, the operator can summon specialists trained in inspections, repairs, and repair assessments.

Though several advantages of embodiments of the present invention are described herein, it should be understood that other advantages and other embodiments of the present invention are within the scope of these descriptions. Indeed, many modifications and other embodiments of the invention set forth herein may come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of testing a structure, the method comprising:
   providing a structure having a front surface and a back surface;
   pressing an ultrasonic transducer device against the front surface of the structure;
   permitting the ultrasonic transducer device to be automatically activated with an activator assembly when the ultrasonic transducer device is pressed against the front surface of the structure;
   emitting an ultrasonic pulse into the structure;
   detecting an echo profile from the structure; and
   activating an indicator if the echo profile includes a return pulse that at least is received from between the front surface and the back surface.

2. A method according to claim 1, wherein pressing an ultrasonic transducer device against the front surface of the structure comprises pressing a coupling element coupled to an ultrasonic transducer into contact with the front surface.

3. A method according to claim 2, wherein the structure has a specific acoustic impedance, wherein the coupling element comprises a material having a specific acoustic impedance that approximately matches the specific acoustic impedance of the structure, and wherein pressing a coupling element coupled to an ultrasonic transducer into contact with the front surface comprises dry-coupling the ultrasonic transducer device to the front surface.

4. A method according to claim 1, wherein pressing an ultrasonic transducer device against the front surface of the structure comprises pressing a switch attached to the ultrasonic transducer device against the front surface.

5. A method according to claim 4, wherein pressing the switch against the front surface causes the ultrasonic transducer device to emit the ultrasonic pulse into the structure.

6. A method according to claim 1, wherein pressing an ultrasonic transducer device against the front surface of the structure comprises simultaneously pressing multiple switches attached to the ultrasonic transducer device against the front surface.

7. A method according to claim 6, wherein the multiple switches partially surround an axis passing through the ultrasonic transducer device.

8. A method according to claim 7, wherein the axis passing through the ultrasonic transducer device comprises an acoustic axis of the ultrasonic transducer device, and wherein simultaneously pressing multiple switches attached to the ultrasonic transducer device against the front surface comprises directing the acoustic axis of the ultrasonic transducer device to be perpendicular to the surface.

9. A method according to claim 1, wherein pressing an ultrasonic transducer device against the front surface of the structure comprises pressing the ultrasonic transducer device against a portion of the front surface, the portion being near an impact site of the front surface.

10. A method according to claim 9, further comprising pressing the ultrasonic transducer device against multiple portions of the front surface, the multiple portions partially surrounding an impact site of the front surface.

11. A method according to claim 1, wherein activating an indicator if the echo profile includes a return pulse that at least is received from between the front surface and the back surface comprises activating an indicator if the echo profile includes a return pulse that at least occurs before an expected time of a return pulse from the back surface.

12. A method according to claim 1, wherein activating an indicator if the echo profile includes a return pulse that at least is received from between the front surface and the back surface comprises automatically activating an indicator if the echo profile includes a return pulse that at least exhibits a time of flight of duration:
  greater than a time of flight corresponding to the front surface; and
  less than a predetermined time of flight corresponding to a predetermined depth defined between the front surface and the back surface.

13. A method according to claim 12, further comprising automatically activating an indicator that indicates no damage if the echo profile does not include a return pulse received from between the front surface and the predetermined depth.

14. A method according to claim 1, wherein activating an indicator if the echo profile includes a return pulse that at least is received from between the front surface and the back surface comprises automatically activating an indicator if the echo profile includes a return pulse that at least exhibits:
  a time of flight of less duration than a predetermined time of flight corresponding to a predetermined depth defined between the front surface and the back surface; and
  an amplitude exceeding a predetermined threshold.

15. A method according to claim 14, further comprising, once an indicator is activated, emitting additional ultrasonic pulses, detecting corresponding additional echo profiles, and continuously activating the indicator as long as detected echo profiles include return pulses that at least exhibit:
  times of flight of less durations than the predetermined time of flight; and
  amplitudes exceeding the predetermined threshold.

16. A diagnostic apparatus for detecting damages in a structure, the apparatus comprising:
  an ultrasonic transducer device configured to be pressed against a structure, the structure having a front surface and a back surface, the ultrasonic transducer device being further configured to emit ultrasonic pulses into the structure through the front surface and detect echo profiles from the structure through the front surface;
  an activator assembly configured to permit automatic activation of the ultrasonic transducer device when the ultrasonic transducer device is pressed against the structure;
  an indicator; and
  an electronic device configured to activate the indicator if the ultrasonic transducer device detects an echo profile that includes a return pulse received from between the front surface and the back surface.

17. A diagnostic apparatus for inspecting a structure through a surface of the structure, the apparatus comprising:
  an ultrasonic transducer device configured to emit ultrasonic pulses and detect return pulses;
  an activator assembly configured to permit automatic activation of the ultrasonic transducer device when the ultrasonic transducer device is pressed against the structure;
  an indicator; and
  an electronic device disposed in electronic communication with each of the ultrasonic transducer device and the indicator, the electronic device configured to automatically activate the indicator if the ultrasonic transducer device detects a return pulse that at least exhibits a time of flight of less duration than a predetermined time of flight.

18. A diagnostic apparatus according to claim 17, wherein the activator assembly comprises at least one switch attached to the ultrasonic transducer device and configured to be actuated when the ultrasonic transducer device is pressed against a surface.

19. A diagnostic apparatus according to claim 18, wherein the activator assembly comprises multiple switches configured to permit activation of the ultrasonic transducer device when all of the multiple switches are actuated simultaneously, wherein the activator assembly is constructed such that all of the multiple switches are simultaneously actuated when the ultrasonic transducer device is pressed against a surface.

20. A diagnostic apparatus according to claim 19, wherein the multiple switches at least partially surround an axis passing through the ultrasonic transducer device.

21. A diagnostic apparatus according to claim 17, wherein the ultrasonic transducer device comprises an ultrasonic transducer and a coupling element coupled to the transducer for disposition between the transducer and a surface of a structure.

22. A diagnostic apparatus according to claim 21, further comprising multiple switches attached to the ultrasonic transducer device and configured to permit activation of the ultrasonic transducer when all of the multiple switches are actuated simultaneously by pressing the coupling element against a surface of a structure.

23. A diagnostic apparatus according to claim 17, wherein the electronic device is configured to automatically activate the indicator if the ultrasonic transducer device detects a return pulse that at least exhibits a time of flight of duration greater than a first predetermined time of flight and less than a second predetermined time of flight.

24. A diagnostic apparatus according to claim 23, wherein the ultrasonic transducer device comprises an ultrasonic transducer and a coupling element for disposition between the transducer and a surface of a structure, wherein the coupling element has a proximal end coupled to the transducer and a distal end for pressing against a surface, and wherein the first predetermined time of flight corresponds approximately to the distal end of the coupling element.

25. A diagnostic apparatus according to claim 17, wherein the electronic device is configured to automatically activate the indicator if the ultrasonic transducer device detects a return pulse that at least exhibits:
- a time of flight of duration greater than a first predetermined time of flight and less than a second predetermined time of flight; and
- an amplitude exceeding a predetermined threshold.

26. A diagnostic apparatus according to claim 25, wherein the electronic device is configured to, once the indicator is activated, continuously activate the indicator as long as the ultrasonic transducer device detects return pulses that at least exhibit:
- times of flight of durations greater than the first predetermined time of flight and less than the second predetermined time of flight; and
- amplitudes exceeding the predetermined threshold.

* * * * *